United States Patent [19]
McGuckin, Jr.

[11] Patent Number: 6,090,118
[45] Date of Patent: Jul. 18, 2000

[54] ROTATIONAL THROMBECTOMY APPARATUS AND METHOD WITH STANDING WAVE

[76] Inventor: James F. McGuckin, Jr., 585 County Line Rd., Radnor, Pa. 19087

[21] Appl. No.: 09/122,483

[22] Filed: Jul. 23, 1998

Related U.S. Application Data

[60] Provisional application No. 60/053,545, Jul. 24, 1997.

[51] Int. Cl.[7] .................................................. A61B 17/22
[52] U.S. Cl. .............................................................. 606/159
[58] Field of Search ...................................... 606/159, 170, 606/180, 127, 128; 604/53, 49

[56] References Cited

U.S. PATENT DOCUMENTS

| | | |
|---|---|---|
| Re. 33,569 | 4/1991 | Gifford et al. . |
| 4,646,736 | 3/1987 | Auth . |
| 4,883,460 | 11/1989 | Zanetti . |
| 4,986,807 | 1/1991 | Farr . |
| 4,994,067 | 2/1991 | Summers . |
| 5,002,553 | 3/1991 | Shiber . |
| 5,007,896 | 4/1991 | Shiber . |
| 5,009,659 | 4/1991 | Hamlin et al. . |
| 5,011,488 | 4/1991 | Ginsburg . |
| 5,011,489 | 4/1991 | Salem . |
| 5,011,490 | 4/1991 | Fischell et al. . |
| 5,019,088 | 5/1991 | Farr . |
| 5,019,089 | 5/1991 | Farr . |
| 5,024,651 | 6/1991 | Shiber . |
| 5,026,383 | 6/1991 | Nobles . |
| 5,026,384 | 6/1991 | Farr et al. . |
| 5,041,217 | 8/1991 | Shiber . |
| 5,042,984 | 8/1991 | Kensey et al. . |
| 5,047,040 | 9/1991 | Simpson et al. . |
| 5,047,041 | 9/1991 | Samuels . |
| 5,049,124 | 9/1991 | Bales . |
| 5,049,154 | 9/1991 | Quadri . |
| 5,053,044 | 10/1991 | Mueller et al. . |
| 5,059,203 | 10/1991 | Husted . |
| 5,061,240 | 10/1991 | Cherian . |
| 5,062,648 | 11/1991 | Gomringer . |
| 5,069,679 | 12/1991 | Taheri . |
| 5,071,424 | 12/1991 | Reger . |
| 5,071,425 | 12/1991 | Gifford et al. . |
| 5,074,841 | 12/1991 | Ademovic et al. . |
| 5,078,722 | 1/1992 | Stevens . |
| 5,078,723 | 1/1992 | Dance et al. . |
| 5,084,010 | 1/1992 | Plaia et al. . |
| 5,085,662 | 2/1992 | Willard . |
| 5,087,264 | 2/1992 | Miller et al. . |
| 5,087,265 | 2/1992 | Summers . |
| 5,092,839 | 3/1992 | Kipperman . |
| 5,092,872 | 3/1992 | Segalowitz . |
| 5,092,873 | 3/1992 | Simpson et al. . |
| 5,097,849 | 3/1992 | Kensey et al. . |
| 5,100,423 | 3/1992 | Fearnot . |
| 5,100,424 | 3/1992 | Jang et al. . |
| 5,100,425 | 3/1992 | Fischell et al. . |
| 5,100,426 | 3/1992 | Nixon . |
| 5,102,415 | 4/1992 | Guenther . |
| 5,108,411 | 4/1992 | McKenzie . |
| 5,108,419 | 4/1992 | Reger et al. . |
| 5,112,347 | 5/1992 | Taheri . |
| 5,114,399 | 5/1992 | Kovalcheck . |
| 5,116,350 | 5/1992 | Stevens . |

(List continued on next page.)

FOREIGN PATENT DOCUMENTS

| | | |
|---|---|---|
| 0177782 | 9/1985 | European Pat. Off. . |
| 0452631 | 2/1991 | European Pat. Off. . |
| 0709110 | 5/1995 | European Pat. Off. . |
| 89004949 U | 1/1989 | Germany . |

*Primary Examiner*—Michael Buiz
*Assistant Examiner*—Kevin Truong
*Attorney, Agent, or Firm*—Charles N. Quinn

[57] ABSTRACT

Apparatus for clearing lumens of thrombolytic material, comprising a motor including a control therefor operable using one hand holding the motor; an elongated wire connected to the motor for rotation by the motor; a catheter for enveloping a length of the wire; and a grip facilitating manual rotation of the catheter by the one hand independently of the wire as the wire is rotated by the motor at a speed sufficient to create a standing wave in a portion of the wire extending from the catheter.

15 Claims, 12 Drawing Sheets

U.S. PATENT DOCUMENTS

| | | |
|---|---|---|
| 5,127,902 | 7/1992 | Fischell . |
| 5,127,917 | 7/1992 | Niederhauser et al. . |
| 5,131,379 | 7/1992 | Sewell . |
| 5,133,725 | 7/1992 | Quadri . |
| 5,135,482 | 8/1992 | Neracher . |
| 5,135,484 | 8/1992 | Wright . |
| 5,135,531 | 8/1992 | Shiber . |
| 5,139,506 | 8/1992 | Bush . |
| 5,141,491 | 8/1992 | Bowald . |
| 5,141,503 | 8/1992 | Sewell . |
| 5,152,771 | 10/1992 | Sabbaghian et al. . |
| 5,152,772 | 10/1992 | Sewell . |
| 5,152,773 | 10/1992 | Redha . |
| 5,154,724 | 10/1992 | Andrews . |
| 5,156,610 | 10/1992 | Reger . |
| 5,158,564 | 10/1992 | Schnepp-Pasch et al. . |
| 5,160,342 | 11/1992 | Reger et al. . |
| 5,163,421 | 11/1992 | Bernstein et al. . |
| 5,170,805 | 12/1992 | Kensey et al. . |
| 5,171,316 | 12/1992 | Mehigan . |
| 5,176,693 | 1/1993 | Pannek . |
| 5,178,625 | 1/1993 | Groshong . |
| 5,181,920 | 1/1993 | Mueller et al. . |
| 5,192,268 | 3/1993 | Shiber . |
| 5,192,290 | 3/1993 | Hilal . |
| 5,192,291 | 3/1993 | Pannek . |
| 5,195,954 | 3/1993 | Schnepp-Pesch et al. ............. 606/159 |
| 5,195,956 | 3/1993 | Stockmeier . |
| 5,196,024 | 3/1993 | Barath . |
| 5,197,483 | 3/1993 | Grooters . |
| 5,201,750 | 4/1993 | Hecherl et al. . |
| 5,209,749 | 5/1993 | Buelna . |
| 5,211,651 | 5/1993 | Reger et al. . |
| 5,211,683 | 5/1993 | Maginot . |
| 5,217,453 | 6/1993 | Wilk . |
| 5,217,474 | 6/1993 | Zacca et al. . |
| 5,222,965 | 6/1993 | Haughton . |
| 5,222,966 | 6/1993 | Perkins et al. . |
| 5,224,945 | 7/1993 | Pannek . |
| 5,224,949 | 7/1993 | Gomringer et al. . |
| 5,226,909 | 7/1993 | Evans et al. . |
| 5,234,450 | 8/1993 | Segalowitz . |
| 5,234,451 | 8/1993 | Ospyka . |
| 5,242,460 | 9/1993 | Klein et al. . |
| 5,242,461 | 9/1993 | Kortenbach et al. . |
| 5,248,296 | 9/1993 | Alliger . |
| 5,250,059 | 10/1993 | Andreas et al. . |
| 5,250,060 | 10/1993 | Carbo et al. . |
| 5,261,877 | 11/1993 | Fine et al. . |
| 5,267,954 | 12/1993 | Nita . |
| 5,269,751 | 12/1993 | Kaliman et al. . |
| 5,269,793 | 12/1993 | Simpson . |
| 5,282,484 | 2/1994 | Reger . |
| 5,282,813 | 2/1994 | Redha . |
| 5,284,478 | 2/1994 | Nobles et al. . |
| 5,284,486 | 2/1994 | Kotula et al. . |
| 5,295,958 | 3/1994 | Shtruman . |
| 5,300,025 | 4/1994 | Wantink . |
| 5,303,719 | 4/1994 | Wilk et al. . |
| 5,304,189 | 4/1994 | Goldberg et al. . |
| 5,304,220 | 4/1994 | Maginot . |
| 5,306,244 | 4/1994 | Shiber . |
| 5,308,354 | 5/1994 | Zacca et al. . |
| 5,312,425 | 5/1994 | Evans et al. . |
| 5,312,427 | 5/1994 | Shturman . |
| 5,314,407 | 5/1994 | Auth et al. . |
| 5,314,438 | 5/1994 | Shturman . |
| 5,318,576 | 6/1994 | Plassche et al. . |
| 5,320,599 | 6/1994 | Griep et al. . |
| 5,320,634 | 6/1994 | Vigil et al. . |
| 5,334,211 | 8/1994 | Shiber . |
| 5,336,167 | 8/1994 | Sullivan et al. . |
| 5,336,234 | 8/1994 | Vigil et al. . |
| 5,342,394 | 8/1994 | Matsuno et al. . |
| 5,344,395 | 9/1994 | Whalen et al. . |
| 5,345,940 | 9/1994 | Seward et al. . |
| 5,346,473 | 9/1994 | Bowman . |
| 5,348,017 | 9/1994 | Thornton et al. . |
| 5,350,390 | 9/1994 | Sher . |
| 5,352,232 | 10/1994 | Cohen . |
| 5,356,418 | 10/1994 | Shturman . |
| 5,358,472 | 10/1994 | Vance et al. . |
| 5,358,485 | 10/1994 | Vance et al. . |
| 5,358,507 | 10/1994 | Daily . |
| 5,358,509 | 10/1994 | Fine et al. . |
| 5,360,432 | 11/1994 | Shturman . |
| 5,360,433 | 11/1994 | Medl . |
| 5,366,463 | 11/1994 | Ryan . |
| 5,366,464 | 11/1994 | Belknap . |
| 5,368,603 | 11/1994 | Halliburton . |
| 5,370,609 | 12/1994 | Drasler et al. . |
| 5,370,651 | 12/1994 | Summers . |
| 5,372,601 | 12/1994 | Lary . |
| 5,383,460 | 1/1995 | Jang et al. . |
| 5,395,311 | 3/1995 | Andrews . |
| 5,395,315 | 3/1995 | Griep . |
| 5,395,384 | 3/1995 | Duthoit . |
| 5,402,790 | 4/1995 | Jang et al. . |
| 5,403,334 | 4/1995 | Evans et al. . |
| 5,409,454 | 4/1995 | Fischell et al. . |
| 5,411,509 | 5/1995 | Hilal . |
| 5,417,703 | 5/1995 | Brown et al. . |
| 5,419,774 | 5/1995 | Willard et al. . |
| 5,423,799 | 6/1995 | Shiu . |
| 5,423,838 | 6/1995 | Willard . |
| 5,429,136 | 7/1995 | Milo et al. . |
| 5,441,510 | 8/1995 | Simpson et al. . |
| 5,449,369 | 9/1995 | Imran . |
| 5,449,372 | 9/1995 | Gelbfish . |
| 5,451,208 | 9/1995 | Goldrath . |
| 5,453,088 | 9/1995 | Boudewijn et al. . |
| 5,476,450 | 12/1995 | Ruggio . |
| 5,480,370 | 1/1996 | La Rosa . |
| 5,490,859 | 2/1996 | Mische et al. . |
| 5,496,267 | 3/1996 | Drasler et al. . |
| 5,501,694 | 3/1996 | Resseman et al. . |
| 5,507,292 | 4/1996 | Jang et al. . |
| 5,507,760 | 4/1996 | Wynne et al. . |
| 5,507,761 | 4/1996 | Duer . |
| 5,512,044 | 4/1996 | Duer . |
| 5,514,115 | 5/1996 | Frantzen et al. . |
| 5,514,150 | 5/1996 | Rostoker . |
| 5,514,151 | 5/1996 | Fogarty et al. . |
| 5,520,635 | 5/1996 | Gelbfish . |
| 5,522,824 | 6/1996 | Ashby . |
| 5,522,825 | 6/1996 | Kropf et al. . |
| 5,522,826 | 6/1996 | Daily . |
| 5,527,323 | 6/1996 | Conley et al. . |
| 5,527,326 | 6/1996 | Hermann et al. . |
| 5,527,327 | 6/1996 | Louw et al. . |
| 5,527,330 | 6/1996 | Tovey . |
| 5,536,242 | 7/1996 | Willard et al. . |
| 5,540,656 | 7/1996 | Pflueger et al. . |
| 5,540,707 | 7/1996 | Ressemann et al. . |
| 5,542,917 | 8/1996 | Nita et al. . |
| 5,547,469 | 8/1996 | Rowland et al. . |
| 5,554,163 | 9/1996 | Shturman . |
| 5,556,405 | 9/1996 | Lary . |
| 5,556,408 | 9/1996 | Farhat . |
| 5,562,701 | 10/1996 | Huiteme et al. . |
| 5,569,204 | 10/1996 | Cramer . |
| 5,569,275 | 10/1996 | Kotula et al. . |

| | | | | | |
|---|---|---|---|---|---|
| 5,569,276 | 10/1996 | Jang et al. . | 5,649,946 | 7/1997 | Bramlet . |
| 5,569,277 | 10/1996 | Evans et al. . | 5,653,722 | 8/1997 | Kieturakis . |
| 5,569,279 | 10/1996 | Rainin . | 5,658,282 | 8/1997 | Daw et al. . |
| 5,571,122 | 11/1996 | Kelly et al. . | 5,658,301 | 8/1997 | Lemaitre et al. . |
| 5,571,130 | 11/1996 | Simpson et al. . | 5,658,302 | 8/1997 | Wicherski et al. . |
| 5,571,167 | 11/1996 | Maginot . | 5,662,603 | 9/1997 | Gelbfish . |
| 5,584,842 | 12/1996 | Fogarty et al. . | 5,662,671 | 9/1997 | Barbut et al. . |
| 5,584,843 | 12/1996 | Wulfman et al. . | 5,662,701 | 9/1997 | Plaia et al. . |
| 5,591,183 | 1/1997 | Chin . | 5,665,093 | 9/1997 | Atkins . |
| 5,591,184 | 1/1997 | McDonnell et al. . | 5,665,098 | 9/1997 | Kelly et al. . |
| 5,601,580 | 2/1997 | Goldberg et al. . | 5,667,480 | 9/1997 | Knight et al. . |
| 5,601,581 | 2/1997 | Fogarty et al. . | 5,669,920 | 9/1997 | Conley . |
| 5,609,602 | 3/1997 | Machemer et al. . | 5,674,226 | 10/1997 | Doherty et al. . |
| 5,616,149 | 4/1997 | Barath . | 5,674,232 | 10/1997 | Halliburton . |
| 5,622,188 | 4/1997 | Plaia et al. . | 5,681,335 | 10/1997 | Serra et al. . |
| 5,624,455 | 4/1997 | Matsuno . | 5,681,336 | 10/1997 | Clement et al. . |
| 5,624,457 | 4/1997 | Farley et al. . | 5,683,362 | 11/1997 | Rowland et al. . |
| 5,626,562 | 5/1997 | Castro . | 5,688,234 | 11/1997 | Frisbie . |
| 5,626,593 | 5/1997 | Imran . | 5,695,506 | 12/1997 | Pike et al. . |
| 5,626,597 | 5/1997 | Urban et al. . | 5,695,507 | 12/1997 | Auth et al. . |
| 5,628,746 | 5/1997 | Clayman . | 5,695,508 | 12/1997 | Chigogidze . |
| 5,628,761 | 5/1997 | Rizik . | 5,695,514 | 12/1997 | Chin . |
| 5,630,823 | 5/1997 | Schmitz-Rode et al. . | 5,697,944 | 12/1997 | Lary . |
| 5,632,755 | 5/1997 | Nordgren et al. . | 5,700,240 | 12/1997 | Barwick et al. . |
| 5,643,199 | 7/1997 | Rowland et al. . | 5,702,412 | 12/1997 | Popov et al. . |
| 5,643,296 | 7/1997 | Hundertmark et al. . | 5,702,413 | 12/1997 | Lafontaine . |
| 5,643,297 | 7/1997 | Nordgren et al. . | 5,843,103 | 12/1998 | Wulfman ................................ 606/159 |
| 5,643,298 | 7/1997 | Nordgren et al. . | 5,882,329 | 3/1999 | Patterson et al. ....................... 606/159 |
| 5,649,941 | 7/1997 | Lary . | | | |

```
                              ┌───┐
                              │ 3 │
                              └─┬─┘
                                │
┌───────────────────────────────┴───────────────────────────────┐
│ Observe dye travel through vein to heart using                │
│ fluoroscope revealing any additional venous blockages         │
└───────────────────────────────┬───────────────────────────────┘
                                │
┌───────────────────────────────┴───────────────────────────────┐
│ Insert wire back into balloon lumen                           │
└───────────────────────────────┬───────────────────────────────┘
                                │
┌───────────────────────────────┴───────────────────────────────┐
│ Inflate balloon to crush venous anastomosis and open          │
│ shunt-vein juncture                                           │
└───────────────────────────────┬───────────────────────────────┘
                                │
┌───────────────────────────────┴───────────────────────────────┐
│ Remove balloon and wire                                       │
└───────────────────────────────┬───────────────────────────────┘
                                │
┌───────────────────────────────┴───────────────────────────────┐
│ Insert second sheath between position of first sheath         │
│ insertion shunt-vein juncture, into clean shunt               │
│ region                                                        │
└───────────────────────────────┬───────────────────────────────┘
                                │
┌───────────────────────────────┴───────────────────────────────┐
│ Re-insert instrument wire without catheter through            │
│ sheath into shunt, through any blockage at shunt-             │
│ artery juncture                                               │
└───────────────────────────────┬───────────────────────────────┘
                                │
┌───────────────────────────────┴───────────────────────────────┐
│ Place angioplasty balloon over wire                           │
└───────────────────────────────┬───────────────────────────────┘
                                │
                              ┌─┴─┐
                              │ 4 │
                              └───┘
```

Push balloon into position within arterial anatomosis at artery-shunt juncture

Remove wire leaving angioplasty balloon in position

Inject contrast radiology dye through balloon lumen vacated by wire

Observe dye travel through artery to heart using fluoroscope revealing any additional arterial blockages Insert wire back into balloon lumen Inflate balloon to crush any arterial anastomosis and open shunt-artery juncture Remove platelet plug and residual arterial anastomosis from shunt-artery juncture by pulling on balloon

Remove balloon, wire and sheath

ROTATIONAL THROMBECTOMY APPARATUS AND METHOD WITH STANDING WAVE

This patent application is based on and entitled to the filing date of U.S. provisional application 60/053,575 filed Jul. 24, 1997 now pending in the name of James F. McGuckin, Jr. and entitled "Rotational-Oscillatory Thrombectomy Device".

FIELD OF THE INVENTION

This invention relates to surgical apparatus for use in clearing recurring thrombosis of hemodialysis grafts.

BACKGROUND OF THE INVENTION AND DESCRIPTION OF THE PRIOR ART

Modern hemodialysis technology enables patients with chronic renal failure to live independently between dialysis treatments. Patients utilize this technology as a means of filtering the toxins from their blood by passing blood out of their body through a hemodialysis machine. The hemodialysis machine removes blood toxins by exposing the blood to dialyzing fluid across a semipermeable membrane, in effect creating an artificial kidney.

In order to properly process a patient's blood a graft is made, preferably in patient's arm. At the site of the graft a shunt is placed to connect an artery having a high rate of blood flow with a vein. The shunt provides a convenient inlet on the artery side for blood requiring dialysis filtration processing; the outlet is located on the vein side for return of dialysis processed blood from the hemodialysis station.

The dialysis shunt, while providing a convenient arrangement for hemodialysis processing, may become inoperable after a period of time due to stenosis caused by the high rate of blood flow through the shunt and repetitive injury at the venous anastomosis. Typically, patients must have these constricting portions of the shunt widened periodically in order to continue hemodialysis processing through the shunt.

Shunt blockage is generally treated through a combination of surgical devices and/or pharmaceutical treatments; these techniques are often cost prohibitive and/or require an incision. For example, pharmaceutical treatments generally employ urokinase which, depending on the amount used, can cost upward of $350.00 per application and possibly cause bleeding complications.

Mechanical thrombolysis apparatus and methods for performing thrombolysis are known, being disclosed in U.S. Pat. No. 4,646,736 to Auth, U.S. Pat. No. 5,078,722 to Stevens and U.S. Pat. No. 5,695,507 to Auth, et al.

The apparatus disclosed in these patents seeks to penetrate thrombolytic structures by introducing, for example in the case of '507, a rotating core wire into the thrombus, seeking to withdraw fibrin from the thrombus into the rotating core wire thereby breaking up the network of the thrombus which is preventing blood flow.

SUMMARY OF THE INVENTION

In one of its aspects this invention provides a method for clearing a surgical shunt or native body lumen of thrombolytic or other undesirable material by puncturing the shunt or native body lumen to form an aperture therein, inserting a rotatable hydrophilic wire into the interior of the shunt or body lumen through the aperture and rotating the wire within the shunt or body lumen preferably at a speed sufficient to create a standing wave in an exposed portion of the wire within the shunt or body lumen to sweep the shunt or body lumen clear of thrombolytic or other undesirable material.

In another of its aspects this invention provides apparatus for clearing shunts and native body lumens of thrombolytic or other undesirable material where the apparatus preferably includes a motor preferably including control means which is preferably operable using one hand while holding the motor. The apparatus further preferably includes an elongated wire connected to the motor for rotation thereby where the wire is rotated preferably at speed sufficient to create a standing wave in the wire to rotationally sweep through the shunt or lumen to be cleared. Optionally and desirably the apparatus further preferably includes a catheter for enveloping a length of the wire and gripping means facilitating manual rotation of the catheter by one hand independently of the wire, as the wire is rotated by the motor, preferably at speed sufficient to create the standing wave in at least a portion of the wire extending from the catheter.

In further aspects of the invention the apparatus preferably includes manually actuable means for selectably connecting the wire to the motor.

Preferably the wire is hydrophilic, is not permanently deformable at room temperature and may be either braided or a single filament; a braided wire is most preferred.

Preferably the extremity of the wire remote from the catheter either is angularly disposed with respect to the remainder of the wire or is J-shaped, curving back towards the motor.

In another of the apparatus aspects of the invention, the extremity of the catheter remote from the motor may be preferably angularly disposed with respect to the remainder of the catheter. The catheter is preferably sufficiently resistant to twisting that torque manually applied to the catheter proximate the motor results in corresponding angular rotary movement of the extremity of the catheter remote from the motor.

When the wire is in the form of a single filament, the extremity of the filament extending from the catheter is preferably at an angle to the axis of the filament.

In yet another of its aspects the invention preferably provides first means communicating with the interior of the catheter for selectably supplying or exhausting fluid to and from the catheter interior.

In yet another aspect of the invention the apparatus may preferably further include a sheath enveloping the catheter and a conduit communicating with the interior of the sheath for selectably supplying or exhausting fluid to and from the sheath interior, externally of the catheter. When such a second conduit is present, the second conduit is preferably movable longitudinally along the wire with the sheath.

The gripping means for the catheter is preferably fixedly connected to the first conduit means communicating with the catheter interior and is preferably rotatable unitarily with the catheter about the wire.

In yet another of the apparatus aspects of the invention, the second conduit, the sheath, the motor, the catheter, the first conduit and the wire are all preferably manually disassemblable from one another preferably without use of tools.

In yet another apparatus aspect of the invention, the apparatus preferably further includes a housing for the motor and the control means, where the housing is adapted for grasping by one hand for operator control of the apparatus and where the wire passes through the housing and emerges from an opposite side thereof.

The motor may be electrically, pneumatically or hydraulically powered; electrical power is preferable.

In yet another of its aspects, the method of the invention further includes moving the rotating wire, with a vibrational node extant therein, axially along the lumen to rotationally sweep thrombolytic or other undesirable material from the shunt or lumen in a circumferentially sweeping action.

In a method aspect of the invention, when the rotatable hydrophilic wire is inserted into the interior of the shunt or lumen there is desirably provided a catheter surrounding the hydrophilic wire from which the wire extends into the interior of the shunt or lumen through the aperture.

In a method aspect of the invention, a rotating step desirably further includes rotating the wire but not the catheter within the shunt or lumen at a speed at which the wire forms at least one vibrational node in the portion of the wire extending from the catheter tip within the shunt or lumen.

Most desirably the method aspect of the invention further includes rotating the wire but not the catheter within the shunt or lumen at a speed from about 100 revolutions per minute to about 10,000 revolutions per minute.

In the method aspect of the invention, wire rotation may be performed manually or by a motor rotating the wire within the shunt or lumen. In either event the wire is preferably rotated at a speed at which the wire forms at least one vibrational node in the portion of the wire within the lumen, most preferably in the portion of the wire extending outwardly of the catheter. The wire is desirably moved along the shunt or lumen longitudinally by moving the motor; orientation of the wire within the shunt or lumen is desirably controlled by rotating the catheter, preferably manually.

The motor is most preferably a hand-held motor; moving the wire along the shunt or lumen is most preferably performed by manually moving the motor. Controlling orientation of the wire is preferably performed by manually rotating the catheter. All of these manual operations are preferably performed using only one hand.

In a method aspect of the invention, the rotating step is preferably performed by rotating the wire within the shunt or lumen along the length of the shunt or lumen for a time sufficient to macerate thrombolytic material within the shunt or lumen and thereby produce a standing column of liquified material therewithin.

In another of its aspects, the invention provides a method for clearing a surgical shunt connecting an artery to a vein and associated portions of said artery and vein of thrombolytic material by initially inserting a needle through a patent's skin and into the shunt, inserting a first wire through the needle, sensing whether the first wire is in the shunt preferably by tactile sensation received via the wire, x-ray inspecting skin preferably where the needle was inserted to determine whether the wire is within the shunt, removing the needle when the wire is determined to be within the shunt, placing a first catheter over the first wire with a catheter discharge orifice within the shunt, removing the first wire leaving the first catheter with the discharge end within the shunt, inserting a second wire through the first catheter into the interior of the shunt, removing the first catheter from the shunt, inserting a sheath over the second wire and into the shunt, removing the second wire, inserting a rotatable instrument wire and an associated surrounding catheter through the sheath and into the shunt, supplying lubricating fluid to the associated catheter interior to lubricate the instrument wire for rotation within the associated catheter, sweepingly rotating the instrument wire, but not the associated catheter, through the shunt to liquify thrombolytic material therein, removing the instrument wire and associated catheter from the sheath, applying suction to the sheath to remove liquid thrombolytic material from the shunt interior, injecting anti-coagulant into the shunt interior through the sheath, removing the instrument wire from the associated catheter, disconnecting the instrument wire from a drive motor associated therewith, re-inserting the instrument wire without the associated catheter through the sheath into the shunt interior and through any blockage at the vein end of the shunt and into the vein, placing an angioplasty balloon over the instrument wire, pushing the angioplasty balloon into position within venous anastomosis at vein-shunt juncture, removing the wire leaving the angioplasty balloon in position within the venous anastomosis at vein-shunt juncture, injecting radiology contrast dye through a lumen of the balloon vacated by removal of the instrument wire therefrom, observing dye travel through the vein to the patient's heart to reveal any venous blockages, inserting the instrument wire back into the balloon lumen, inflating the balloon to crush any venous anastomosis and open shunt-vein juncture, removing the balloon and instrument wire from the sheath, inserting a second sheath between the position of first sheath insertion and shunt-vein juncture into a shunt interior region cleansed of thrombolytic material, re-inserting the instrument wire without the associated catheter through the second sheath into the shunt through any blockage at shunt-artery juncture, placing an angioplasty balloon over the wire, pushing the balloon into position within arterial anastomosis at artery-shunt juncture, removing the wire leaving the angioplasty balloon in position, injecting contrasting radiology dye through the balloon lumen vacated by the wire, observing travel of the dye through the artery to the heart thereby revealing any arterial blockages, inserting the instrument wire back into the balloon lumen, inflating the balloon to crush any arterial anastomosis and thereby open shunt-artery juncture, removing a platelet plug and residual arterial anastomosis from the shunt-artery juncture by pulling on the balloon and, finally, removing the balloon, wire and sheath from the patient.

The apparatus may include a hydrophilic wire which is placed into the shunt access port, advanced to the blockage within a lubricated catheter which is steerable and is rotated, with the same hydrophilic wire extending beyond the tip of the directional catheter about its longitudinal axis thereby separating material adhering to the inside surface of the dialysis shunt and mechanically macerating the thrombus.

During rotation, the exposed length of the hydrophilic wire preferably begins to periodically flex in an oscillatory fashion, forming a standing wave contributing to the ability to clear the length of the shunt. The maximum deflection points of the rotating wire allow shunt cleansing by rotating the oscillatory wire providing a scouring action clearing the wall of adherent thrombus while also breaking up clots within the graft. The tip of the hydrophilic wire is preferably translated into and out of the thrombus within the shunt thereby mechanically disrupting and dissolving clots in both directions of translation and hence decreasing time necessary to complete thrombolysis. The wire can then be disassembled from the device and used as necessary to complete a shunt renewal procedure.

In another of its aspects the invention provides a method for clearing dialysis shunts. A catheter entrance port is prepared for reception of the hydrophilic wire apparatus. The tip of the wire is advanced into the clot; the wire is rotated preferably by an electric motor such that the hydrophilic wire rotates about its longitudinal axis within a lubricated catheter, with rotation of the wire creating an oscillatory flexing of the hydrophilic wire along substantially its length outside of the lubricating directional catheter.

DETAILED DESCRIPTION OF THE PREFERRED EMBODIMENT

This invention provides a surgical apparatus and method for clearing of dialysis shunt blockages in hemodialysis patients. Part of the surgical apparatus rotates, separating the blockage material from the inside surface of the dialysis shunt while macerating any thrombus within the shunt. Thus, the shunt is cleared with a minimum of trauma and without use of costly pharmaceuticals.

Figure 1A:
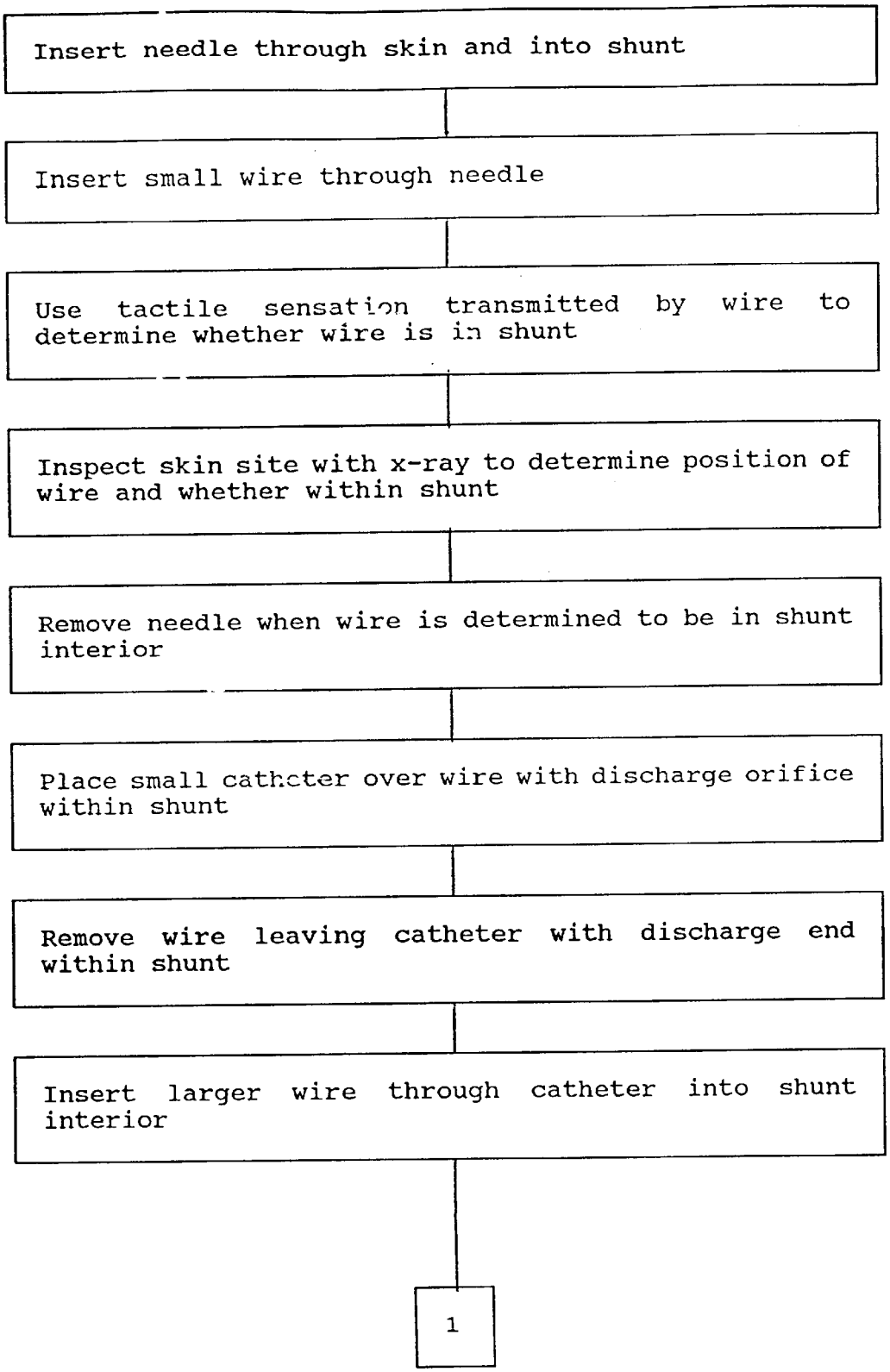
FIG. 1 which is presented as FIGS. 1(a) through 1(f) in separate pages, is a flow chart of a surgical method on invention.
Figure 1B:
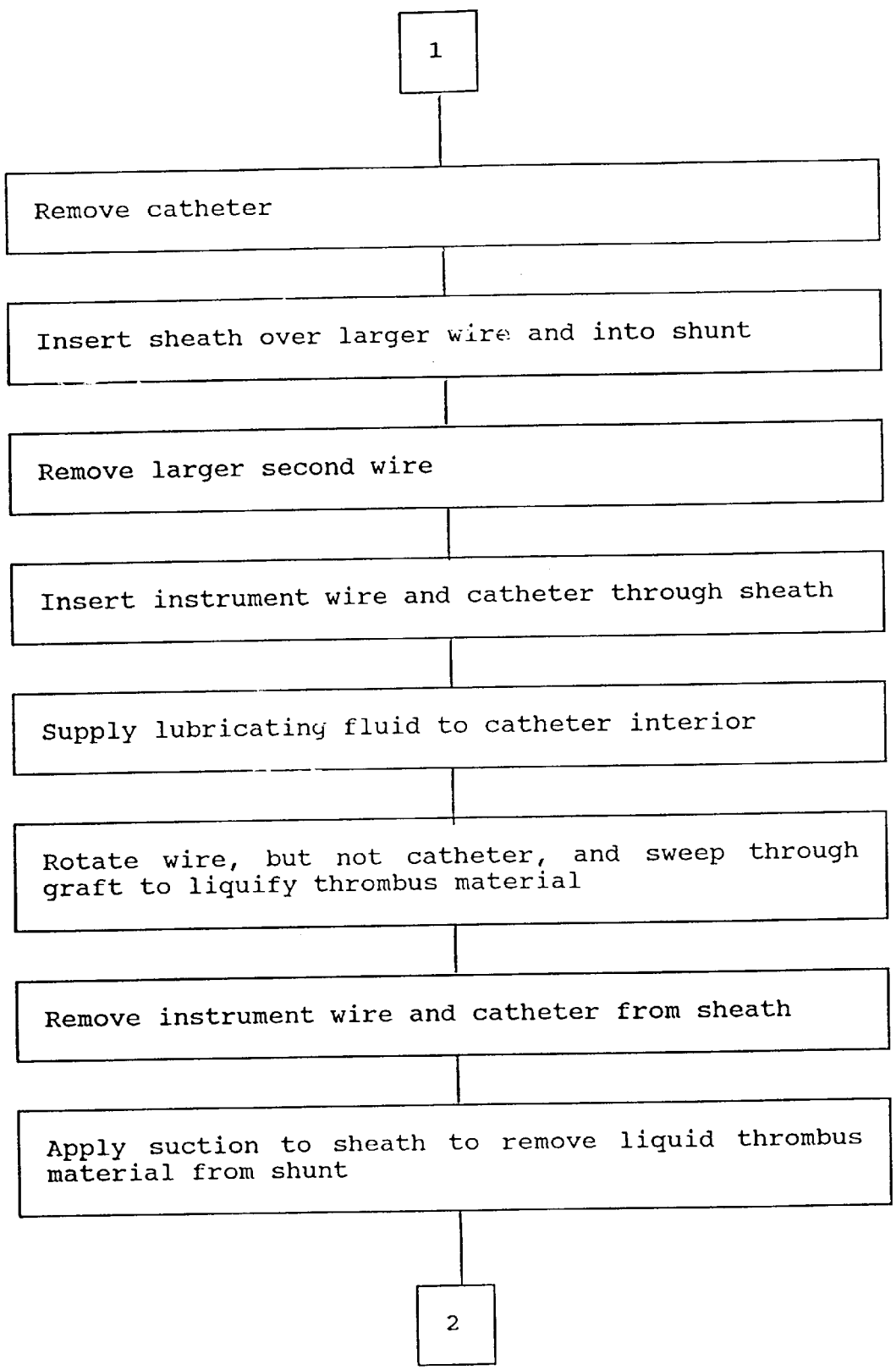
Figure 1C:
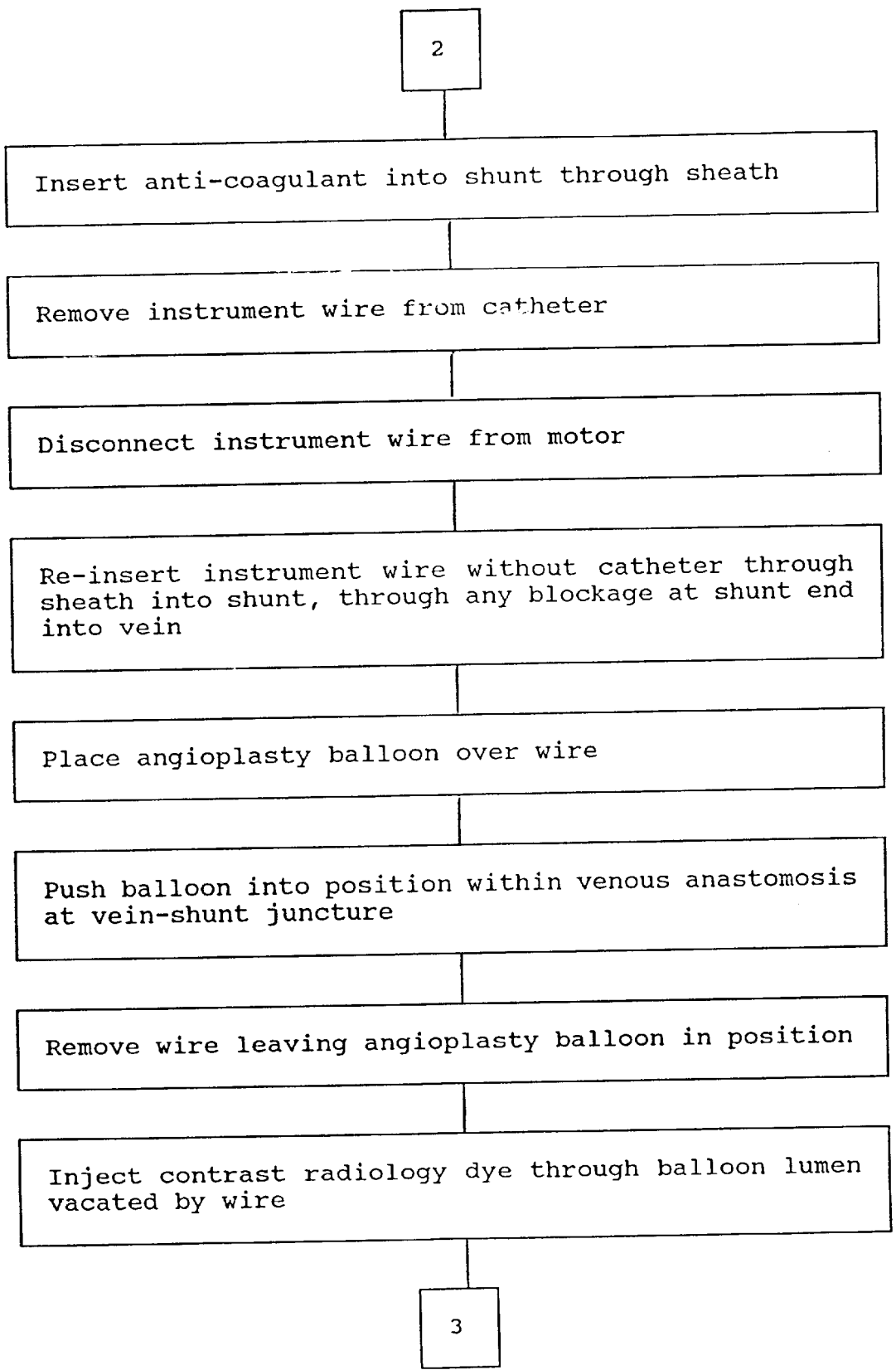
Figure 1F:
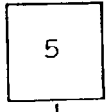
Figure 2:
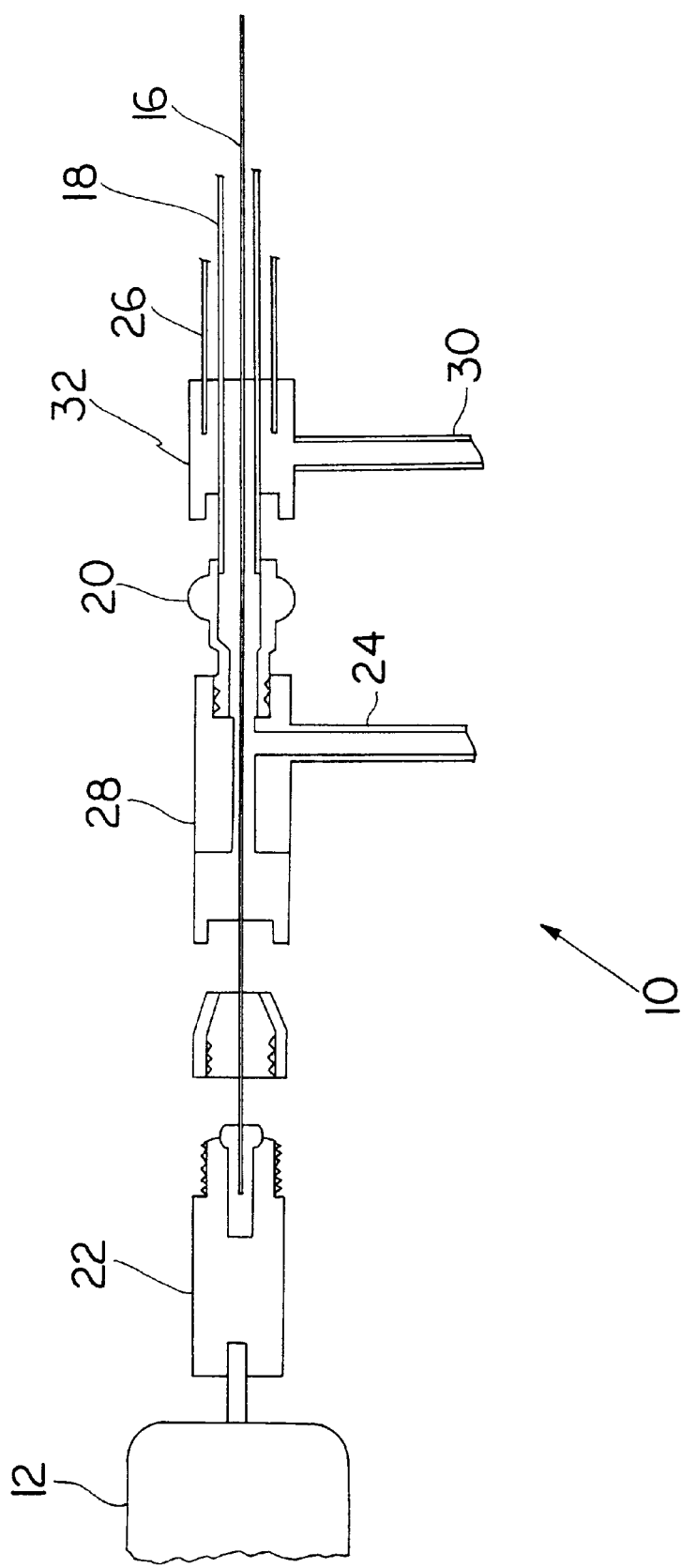
FIG. 2 is a partially exploded side sectional view of one embodiment of apparatus manifesting aspects of the invention.
Figure 3:
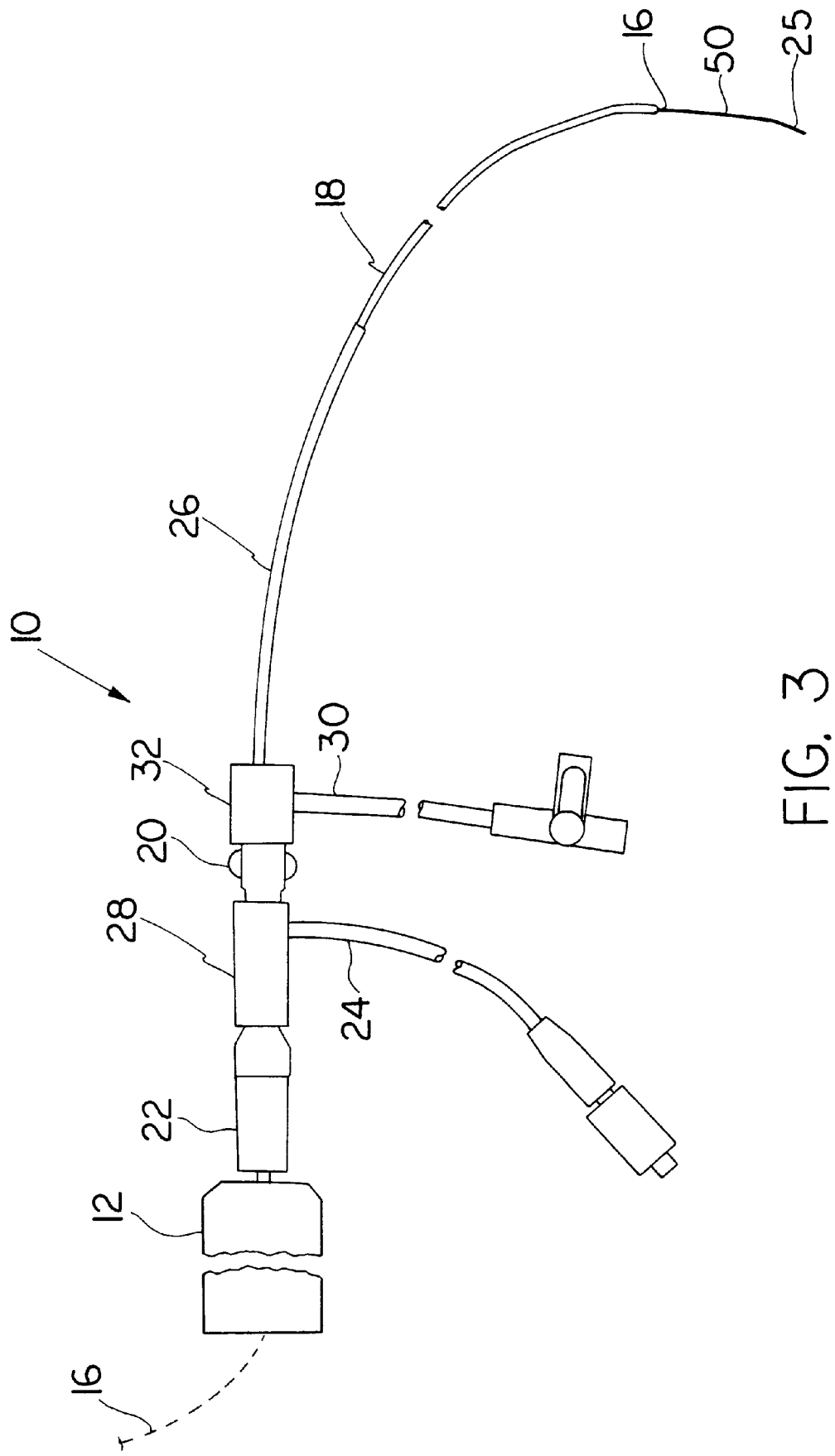
FIG. 3 is an unexploded top view of the apparatus shown in FIG. 2.
Figure 4:
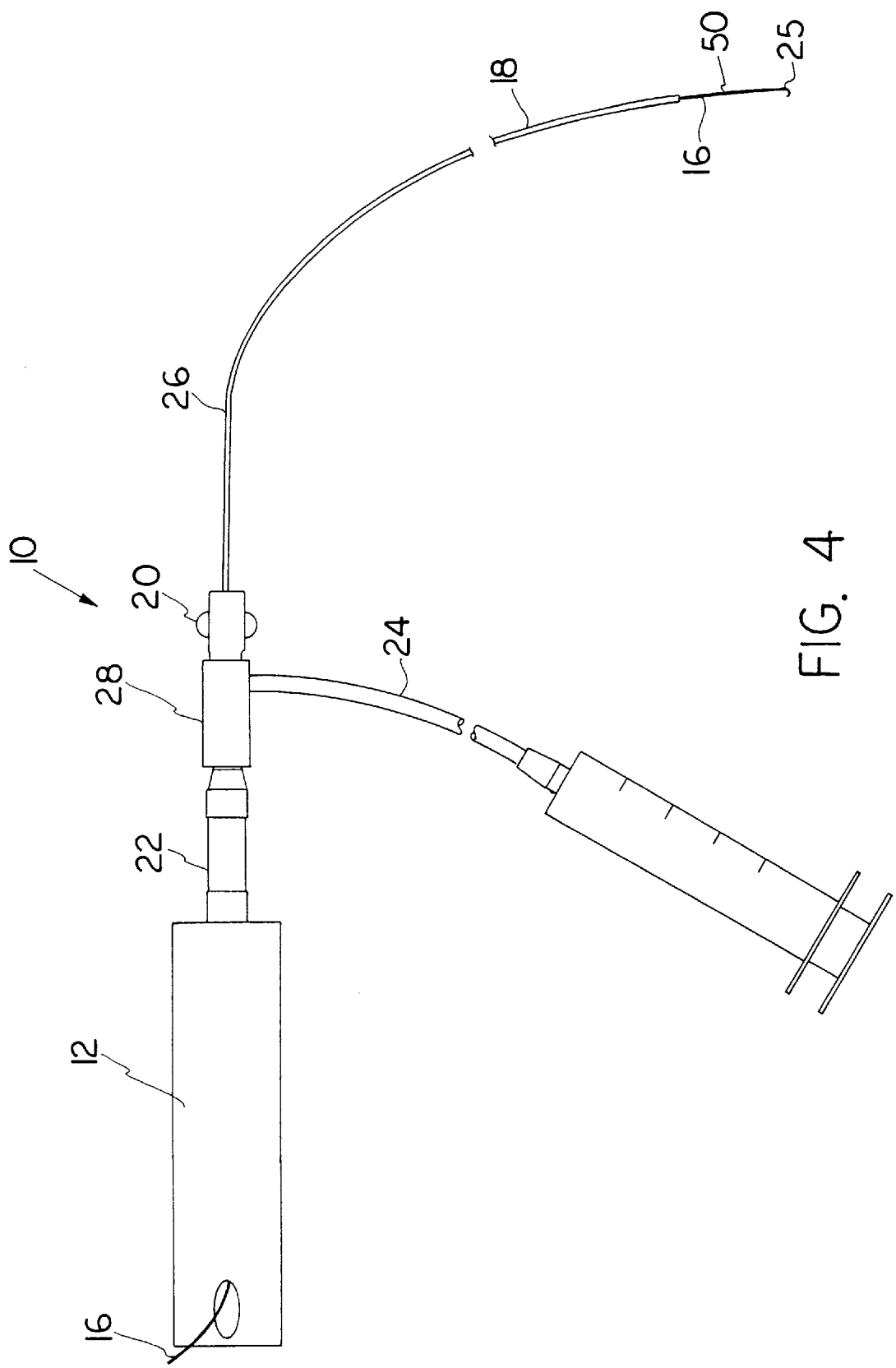
FIG. 4 is a top view of a second embodiment of apparatus in which the rotating wire extends through the handpiece.

Referring to FIG. 2 through 4, the surgical apparatus in accordance with the invention is generally designated 10 and includes a rotatable hydrophilic wire 16 and with a deformed tip 25.

Wire 16 rotates about an axis 11. Rotation of wire 16 of apparatus 10 is preferably performed by an electric motor 12, equipped with a mechanical hand control. However, wire 16 may be turned by pneumatic or hydraulic motor or even manually.

Hydrophilic wire 16 is preferably selected such that it rotates and oscillates so that a maximum number of points of maximum deflection between nodes of the standing wave reach the inner shunt wall to scour and remove adherent thrombus.

Apparatus 10 may be utilized to perform a number of procedures. Wire 16 is advanced through a catheter entrance port 52 of a dialysis shunt 34. Wire 16 is advanced along the interior surface of shunt 34 in the direction of a blockage; the tip of wire 16 may be translated into a thrombus, extending out of a distal tip of a directional lubricated catheter by the operator handling apparatus 10. As wire tip 25 rotates about axis 11, an adherent clot is separated from the interior surface 54 of dialysis shunt 34 by rotating contact of deformable wire tip 25 as well as oscillatory flexing of wire 16 in both directions along the longitudinal axis of the shunt as a standing wave is desirably formed in wire 16.

The clot material is broken up by rotation of wire 16 sufficiently such that passage of clot material does not present a physiological problem for the patient; alternatively the clot material may be aspirated out of the shunt via an access port.

Referring to FIGS. 2, 3 and 4, motor 12 preferably includes control means for the motor which is operable using the hand which holds the motor. One hand preferably grasps motor 12 and operates the control means therefor. Elongated wire 16, which is also sometime called the instrument wire, is connected to motor 12 for rotation thereof by motor 12. A catheter 18 envelops wire 16. The tubular gripping means 20 fits about catheter 18 to facilitate manual rotation of catheter 18. A manually chuck 22 provides means for selectively connecting wire 16 to motor 12.

A first conduit 24 is provided communicating with the interior of catheter 18 via a first fitting 28 which connects the first conduit to the interior of catheter 18. A second conduit 30 provides communicating with the interior of sheath 26 via a second fitting 32 providing such connection. A surgical shunt 34 is provided between the vein and artery of the patient to under dialysis.

The apparatus illustrated in FIGS. 2 and 3, motor 12 turns wire 16 while catheter 18 is rotated by manually actuating gripping means 20. Gripping means 20 together with fitting 28 is moveable axially along wire 16 to control the amount of wire 16 which is exposed beyond the extremity of catheter 18.

In the embodiment of the apparatus illustrated in FIG. 4, wire 16 desirably extends out the rear of a housing for motor 12. This facilitates withdrawal of wire 16 to and from the shunt, artery and vein of interest.

In the embodiment illustrated in FIG. 4, a second fitting 32 has not been provided nor has a second conduit been provided for input of fluid to interior of sheath 26.

The portion of wire 16 which is exposed beyond the tip of catheter 18 is designated 50 in the drawings.

Not only is first fitting 28 and first conduit 24 moveable together with gripping means 20 with catheter 18 respecting wire 16 but also second fitting 32 and second conduit 30 are preferably moveable with sheath 26 relative to wire 16.

The extremity of wire 16 remote from the catheter, denoted 50 in the drawings, may be angularly disposed with respect to the remainder of the wire. Alternatively, extremity 50 and wire 16 remote from the tip bend of the catheter may be J shaped.

The extremity portion of catheter 18 remote from motor 12 may be angularly disposed with respect to the remainder of the catheters; this configuration helps positioning of exposed portion of wire 16 by manual movement of catheter 18.

Preferably, second conduit 30, second fitting 32, sheath 26, motor 12, catheter 18, first conduit 24, fitting 28 and wire 16 are all manually disassemblable from one another.

Figure 5:
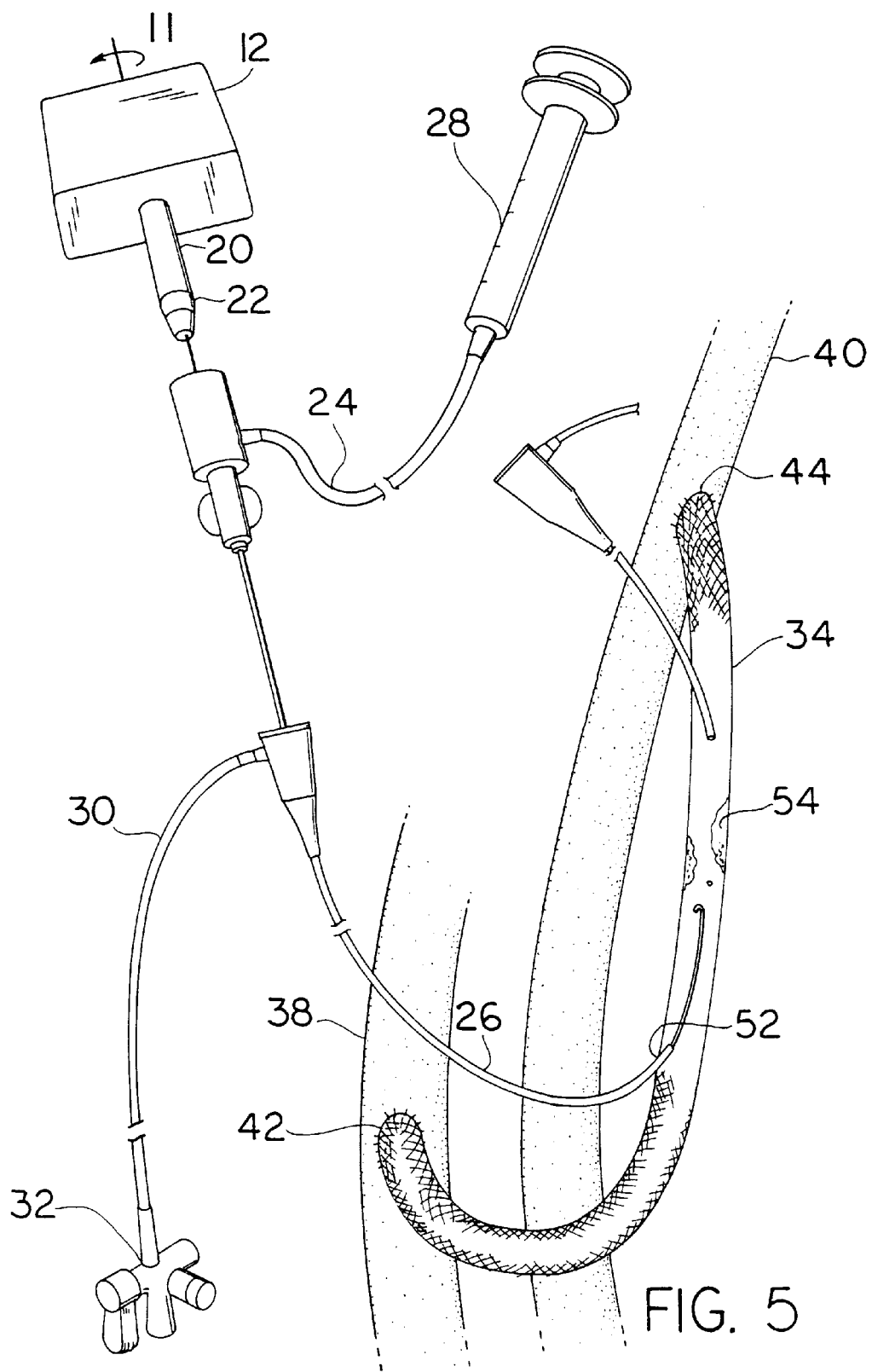
FIG. 5 illustrates apparatus in accordance with the invention in place within a dialysis shunt.

FIG. 5 depicts the apparatus according to one of the aspects of the invention in place within a surgical dialysis shunt where the shunt is denoted generally 34 and connects a vein 38 with an artery 40. Vein shunt-juncture is denoted 42 while artery shunt-juncture is denoted 44.

Figure 8:
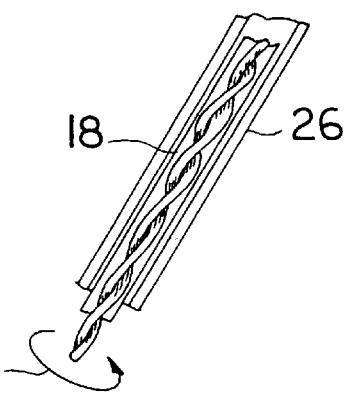
FIG. 8 depicts rotation of the wire in the catheter.

In the practice of the method of the invention for clear a lumen or shunt of thrombolytic material, rotatable hydrophilic wire 16 is inserted into the interior of the shunt or lumen through a suitable aperture which may be created by puncturing the shunt or lumen with a needle. The wire is then rotated within the lumen at a speed of which the wire forms at least one vibrational node in the portion of the wire within the lumen; this configuration of the wire is depicted in FIG. 8. The wire is preferably moved with the vibrational nodes therein axially along the lumen to rotational sweep the thrombolytic material from the lumen; this motion is depicted by arrow A in FIG. 8. Preferably not only the wire but also the catheter extremity is inserted into the lumen through the selected aperture. When the wire is rotated, the catheters maintain stationary relative to the wire and are manually manipulated in order to guide the wire through the shunt and, as necessary, into the shunt-vein or shunt-artery juncture and in the course of performing the most comprehensive aspect of the method of the invention, into the vein or artery to cleanse thrombolytic material therefrom.

The wire is preferably rotated at a speed at which the wire forms at least one vibrational node and the portion 55 of wire 16 extending from catheter 18 into the lumen or shunt. All of this is performed while grasping motor 12 with one hand. Motor 12 preferably has a control by the thumb or forefinger of the hand holding motor 12 so that by using a single hand, the physician or other attending health professional can control not only rotation of wire 16 but also position of catheter 18 thereby controlling the position of wire 16 within the shunt or other lumen to be cleansed. This frees the second hand of the operator to supply medication or lubricant through conduits 24 or 30 or to perform other activity.

As illustrated in FIG. 8, the wire 16 is preferably braided and is rotated in a direction to resist untwisting of the braid.

Figure 6:
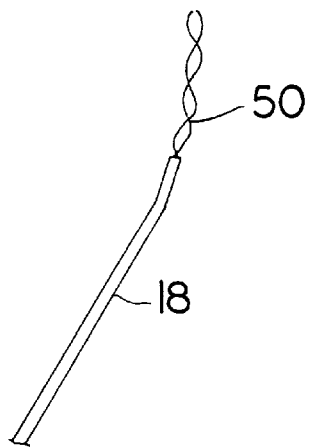
FIG. 6 is a broken view illustrating an embodiment the catheter with a bent end to facilitate directional control of the wire.
Figure 7:
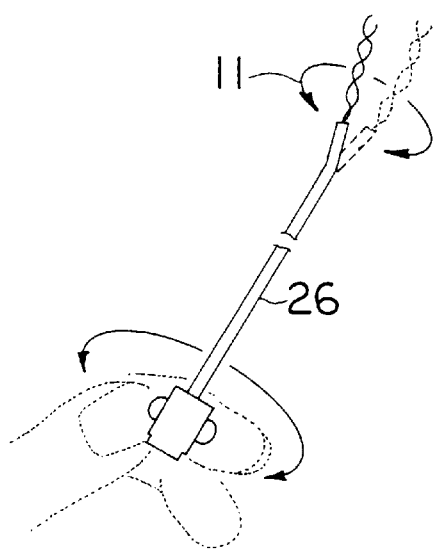
FIG. 7 is a schematic illustrating depicting hand operation of the apparatus in accordance with the invention.
Figure 9:
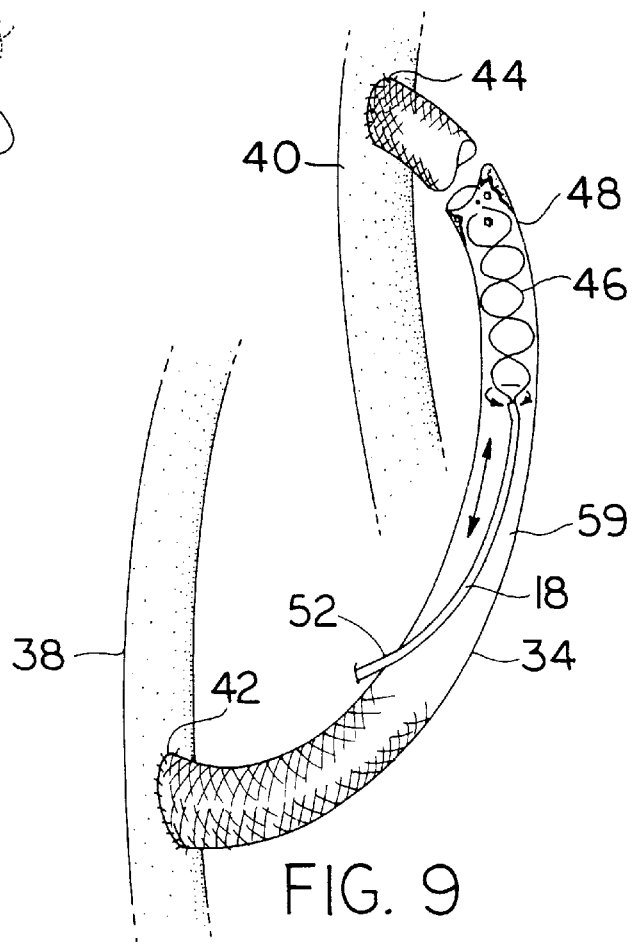
FIG. 9 shows the standing wave formed by the wire resident in this shunt.
Figure 10:
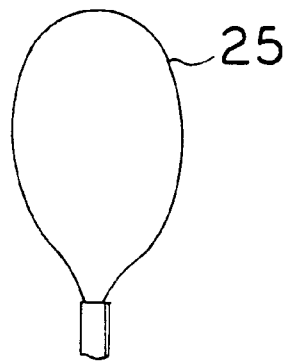
FIGS. 10 through 13 are alternative tip configurations of the rotating wire.
Figure 12:
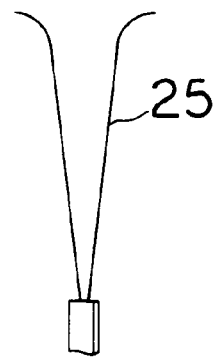
Figure 11:
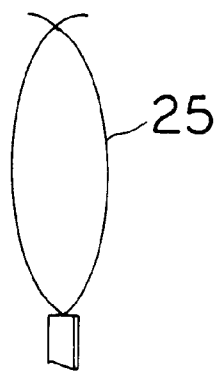
Figure 13:
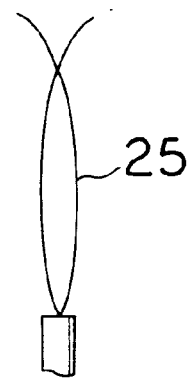

Manual manipulation of the catheter is illustrated in FIG. 7. The angular tip of the catheter 18 when rotated by hand as illustrated permits accurate and close positioning of exposed portion 50 of rotating wire 16. The preferred angular orientation of catheter 18 is illustrated in FIG. 6.

Catheter 18 is preferably sufficiently resistive to twisting the torque manually applied to the catheter approximate to motor, for example via gripping means 20, causes corresponding angular movement of the extremity of the catheter remote from the motor.

While a braided wire is preferable, a filament wire may be used.

The motor is preferably operated to rotate the wire at a speed to create at least one vibrational node therein. The rotation speed of the wire may be from about 100 revolutions per minute to about 10,000 revolutions per minute. The motor used to turn the wire is desirably electrically powered but may also be pneumatically or hydraulically powered. Also, the wire 16 may be rotated manually if necessary.

Not only does the invention have utility with respect to cleansing of dialysis shunts and the juncture of such shunts with veins and arteries, the invention also has utility in cleansing such arteries and veins blockages all the way to the heart.

This comprehensive shunt/vein/artery cleansing procedure begins with inserting a needle through skin and into the shunt. The next step is that of inserting a small wire through the needle. The next step is that of using the tactile sensation transmitted by the wire, determine whether the wire is in the shunt. The next step is that of inspecting the skin site with x-ray to determine position of the wire and whether it is within the shunt.

The next step is that of removing the needle when the wire is determined to be in the shunt interior. The next step is that of placing a small catheter over wire with the discharge orifice within the shunt. The next step is that of removing the wire leaving the catheter with its discharge end within the shunt.

The next step is that of inserting a larger wire through the catheter into the shunt interior. The next step is that of removing the catheter. The next step is that of inserting a sheath over the larger wire and into the shunt.

The next step is that of removing the larger second wire. The next step is that of inserting an instrument wire and the catheter through the sheath. The next step is that of supplying lubricating fluid to the catheter interior.

The next step is that of rotating the wire, but not the catheter, and sweeping through the graft to liquify thrombus material therein. The next step is that of removing the instrument wire and the catheter from sheath. The next step is that of applying suction to the sheath to remove liquid thrombus material from the shunt.

The next step is that of inserting a anti-coagulant into the shunt through sheath. The next step is that of removing the instrument wire from the catheter. The next step is that of disconnecting the instrument wire from the motor.

The next step is that of re-inserting the instrument wire without the catheter through the sheath into the shunt, through any blockage at the shunt end into the vein. The next step is that of placing an angioplasty balloon over the wire. The next step is that of pushing a balloon into position within venous anastomosis at vein-shunt juncture. The next step is that of removing the wire leaving the angioplasty balloon in position.

The next step is that of injecting contrast radiology dye through the balloon lumen vacated by the wire. The next step is that of observing dye travel through the vein to the heart using a fluoroscope revealing any additional venous blockages. The next step is that of inserting a wire back into the balloon lumen. The next step is that of inflating the balloon to crush venous anastomosis and open the shunt-vein juncture.

The next step is that of removing the balloon and wire. The next step is that of inserting a second sheath between position of the first sheath insertion and shunt-vein juncture, into clean shunt region. The next step is that of re-inserting the instrument wire without the catheter through the sheath into the shunt, through any blockage at the shunt-artery juncture. The next step is that of placing an angioplasty balloon over the wire.

The next step is that of pushing the balloon into position within arterial anastomosis at artery-shunt juncture. The next step is that of removing the wire leaving the angioplasty balloon in position. The next step is that of injecting contrast radiology dye through the balloon lumen vacated by the wire.

The next step is that of observing dye travel through the artery to the heart using a fluoroscope and revealing any additional arterial blockages. The next step is that of inserting a wire back into the balloon lumen.

The next step is that of inflating the balloon to crush any arterial anastomosis and open the shunt-artery juncture. The next step is that of removing a platelet plug and residual arterial anastomosis from the shunt-artery juncture by pulling on the balloon. The final step is that of removing the balloon, wire and the sheath.

I claim the following:

1. Apparatus for clearing lumens of thrombolytic material, comprising:
   a. a motor including control means therefor operable using one hand holding said motor;
   b. an elongated wire connected to said motor for rotation thereof by said motor;

c. a catheter for enveloping a length of said wire; and d. gripping means facilitating manual rotation of said catheter by said one hand independently of said wire as said wire is rotated by said motor at a speed sufficient to create a standing wave in a portion of said wire extending from said catheter;

e. first conduit means communicating with the interior of said catheter for selectably supplying or exhausting fluid to and from said catheter interior;

f. a sheath enveloping said catheter; and g. second conduit means communicating with the interior of said sheath for selectably supplying or exhausting fluid to and from said sheath interior externally of said catheter, said second conduit means being movable longitudinally along said wire with said sheath.

2. Apparatus of claim 1 further comprising manually actuable means for selectably connecting said wire to said motor.

3. Apparatus of claim 2 wherein said gripping means is fixedly connected to said first conduit means communicating with said catheter interior and rotatable unitarily therewith about said wire.

4. Apparatus of claim 1 wherein said wire is hydrophilic.

5. Apparatus of claim 1 wherein said wire is not permanently deformable at room temperature.

6. Apparatus of claim 1 wherein the extremity of said wire remote from said catheter is angularly disposed with respect to the remainder of said wire.

7. Apparatus of claim 1 wherein the extremity of said catheter remote from said motor is angularly disposed with respect to the remainder of said catheter.

8. Apparatus of claim 1 wherein said catheter is sufficiently resistive to twisting that torque manually applied to said catheter proximate said motor results in angular movement of the extremity of said catheter remote from said motor.

9. Apparatus of claim 1 wherein the extremity of said wire remote from said catheter is J-shaped.

10. Apparatus of claim 1 wherein said wire is braided.

11. Apparatus of claim 1 wherein said wire is a filament.

12. Apparatus of claim 11 wherein the extremity of said filament extending from said catheter is at an angle to an axis of said filament.

13. Apparatus of claim 12 wherein said second conduit, said sheath, said motor, said catheter, said first conduit and said wire are all manually disassemblable from one another.

14. Apparatus of claim 1 further comprising a housing for said motor and said control means, adapted for grasping by said one hand, wherein said wire passes through said housing and emerges from opposite sides thereof.

15. Apparatus of claim 1 wherein said motor is electrically powered.

* * * * *